(12) United States Patent
Swedberg et al.

(10) Patent No.: US 7,281,942 B2
(45) Date of Patent: Oct. 16, 2007

(54) RELEASABLE WIRE CONNECTOR

(75) Inventors: Benjamin D. Swedberg, Sycamore, IL (US); Gary C. Bethurum, Murrieta, CA (US)

(73) Assignee: IDEAL Industries, Inc., Sycamore, IL (US)

( * ) Notice: Subject to any disclaimer, the term of this patent is extended or adjusted under 35 U.S.C. 154(b) by 0 days.

(21) Appl. No.: 11/561,135

(22) Filed: Nov. 17, 2006

(65) Prior Publication Data

US 2007/0123091 A1    May 31, 2007

Related U.S. Application Data

(60) Provisional application No. 60/737,953, filed on Nov. 18, 2005.

(51) Int. Cl.
*H01R 4/24*    (2006.01)
(52) U.S. Cl. ...................................................... 439/441
(58) Field of Classification Search ......... 439/395–417
See application file for complete search history.

(56) References Cited

U.S. PATENT DOCUMENTS

| | | | | |
|---|---|---|---|---|
| 4,566,748 A | * | 1/1986 | Tanishi et al. | 439/441 |
| 5,158,475 A | * | 10/1992 | Tyler | 439/439 |
| 5,454,730 A | * | 10/1995 | Tozuka | 439/438 |
| 6,746,286 B2 | * | 6/2004 | Blaha | 439/440 |
| 7,063,557 B2 | * | 6/2006 | Ziemke et al. | 439/417 |
| 2002/0155750 A1 | * | 10/2002 | Beege et al. | 439/441 |

* cited by examiner

*Primary Examiner*—Briggitte R Hammond
(74) *Attorney, Agent, or Firm*—Cook, Alex, McFarron, Manzo, Cummings & Mehler, Ltd.

(57) ABSTRACT

A releasable wire connector has a housing and a cap slidably engaging one another and enclosing an electrical contact. The contact has inner and outer flexible fingers disposed opposite wire ports in the housing and cap. The fingers engage conductors inserted into the connector to retain the connectors therein and electrically connect them. The cap carries a release block which will engage some of the fingers and urge them out of engagement with the conductors to allow disengagement of a wire from the connector. One of the fingers may be split into sacrificial and main tines which are arranged so that the sacrificial tine will always be the first to make and the last to break contact with a conductor. Any arcing that may occur will then always be on the sacrificial tine so the main tine will not be degraded by arcing.

23 Claims, 9 Drawing Sheets

RELEASABLE WIRE CONNECTOR

CROSS-REFERENCE TO RELATED APPLICATION

This application claims the benefit of U.S. Provisional Application Ser. No. 60/737,953, filed Nov. 18, 2005.

BACKGROUND OF THE INVENTION

This invention relates to wire connectors and is particularly concerned with a push-in wire connector in which at least one of the wire holding mechanisms is releasable.

There are numerous instances in electrical circuits where a circuit element fails and needs replacing. Ballasts for fluorescent light fixtures are but one example of a circuit element whose life is shorter than other parts of the circuit. Replacing such worn out circuit elements traditionally has required a relatively time consuming procedure wherein wires to the failed device are cut and connections of the remaining, existing wiring to the wires of a new device must be made individually. The time and cost of such procedures could be reduced if the spent device were connected to the circuit by one or more wire connectors that are both releasable and reusable. Then the spent device could simply be disconnected from the circuit and the wires of a new device could be attached to the connector or connectors. U.S. Pat. No. 3,324,447 in FIG. 5 shows a releasable connector which provides a slot for receiving a separate wire release tool that pushes back a wire engaging spring clip. The present invention provides a releasable connector that does not require use of separate tool because the release mechanism is built into the connector.

Another difficulty with releasable, reusable wire connectors is very often the removal of a spent device and the replacement with a new one must be done in a live circuit. Thus, when old wires are removed and new wires are inserted into a connector, the contacts of the connector are subject to arcing as they break and make contact with the wires of an energized circuit. The arcing leads to serious degradation of the contacts which can cause them to fail after only a small number of insertions and removals of wires. The present invention provides a contact for a releasable wire connector that is not subject to premature failure due to arcing.

SUMMARY OF THE INVENTION

The present invention concerns a releasable and reusable wire connector.

A primary object of the invention is a releasable wire connector having an enclosure surrounding a contact and a release mechanism built into the enclosure.

Another object of the invention is a wire connector of the type described including a contact having at least one flexible finger for engaging a conductor inserted into the enclosure. The finger is split to define a main tine and a sacrificial tine. The sacrificial tine is arranged such that it is first to make and last to break contact with a conductor moved into and out of the enclosure, thereby exposing the sacrificial tine to all potential arcing and preventing any arcing to the main tine.

A further object of the invention is a wire connector having a release mechanism including a slidable cap that, once moved to an actuated position, will remain in the actuated position until the user moves it back to a retracted position.

Yet another object of the invention is a wire connector which provides electrical isolation such that wires can be removed from the connector with no fear of anything coming into electrical contact with live circuit components during removal of the wires.

The connector has an enclosure which includes a housing and a cap. The housing has at least one compartment defined therein. The housing has a wire port defined at one end and opening into the compartment. The opposite end of the housing is generally open. The cap is slidably engaged with the housing at its open end. The cap also has a wire port defined therein which opens in alignment with the compartment. Each wire port receives one of the wires of a pair to be connected. A contact is mounted in the compartment. The contact has a pair of flexible fingers, one opposite each wire port. The finger is angled with respect to the axis of the wire port. A stripped end of a wire inserted into a wire port flexes the finger as the wire moves past the finger. Thus, the wire is engaged by the finger opposite each port. The finger is biased against the wire which prevents the wire from disengaging the finger. Any tendency of the wire to back out of the wire port merely increases the gripping force of the finger on the wire.

The cap has at least one inwardly facing plunger formed on it. The plunger is disposed opposite the contact finger at the cap end of the enclosure. The plunger is movable with the cap to selectively engage the finger to bias the finger away from an inserted wire. This releases the pressure of the finger on the wire, allowing the wire to be disengaged from the enclosure. One of the cap or the housing may have a holding feature built into it which will retain the cap in the actuated position until the user has removed the old wire and inserted a new one. Then the user moves the cap out of the actuated position to a retracted position. This permits one-handed operation of the connector.

In a preferred embodiment the contact finger is split into a sacrificial tine and a main tine. The sacrificial tine is the only one subject to arcing because it is the first to make contact with a conductor during insertion and the last to break contact with a conductor during removal.

DETAILED DESCRIPTION OF THE INVENTION

Figure 1:
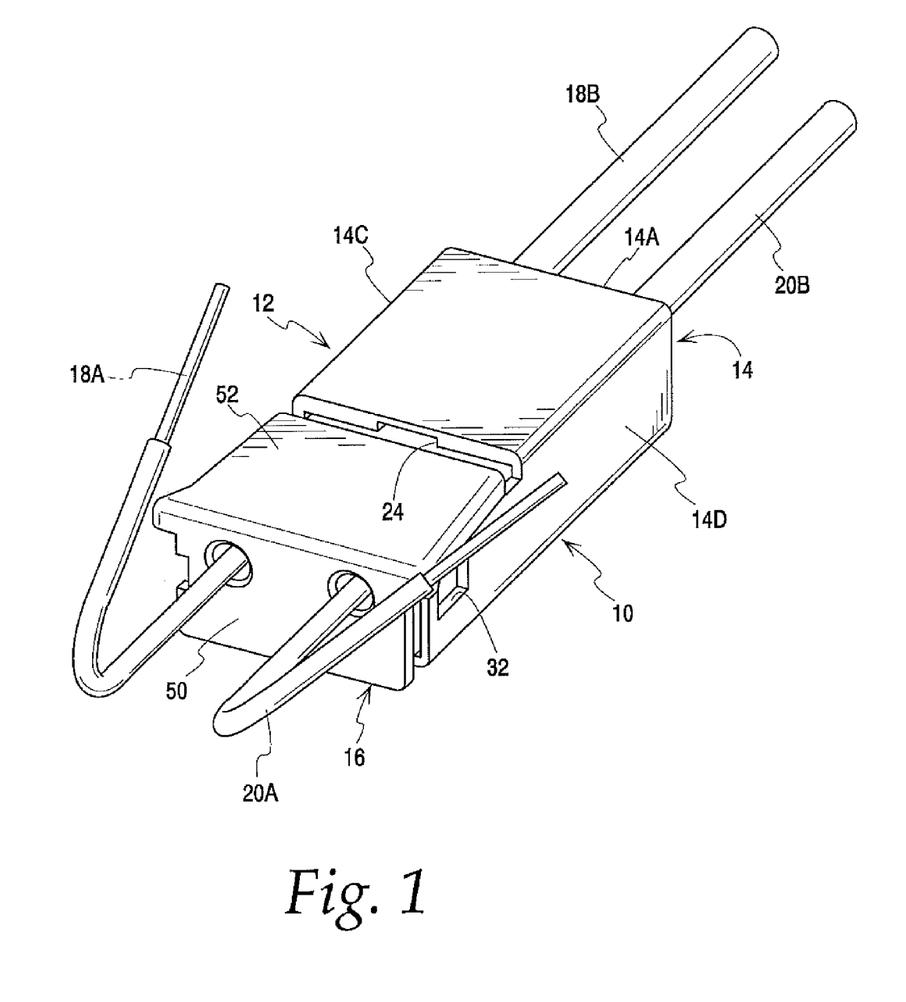
FIG. 1 is perspective view of the wire connector of the present invention, with two pairs of wires installed therein.

FIG. 1 illustrates the wire connector of the present invention generally at 10. The wire connector joins pairs of wires in an in-line configuration with push-in connections. That is, the ends of wires to be connected have their insulation stripped to expose bare conductors. The bare conductors are pushed into the connector 10. A contact in the connector engages the conductors and provides a conductive path between them.

The connector has a generally hollow enclosure 12. The enclosure includes a housing 14 and a cap 16. The cap is slidably mounted on the housing between actuated and retracted positions. The cap is shown in FIG. 1 in the retracted position. The interior of the cap includes a release block which will be described in detail below. Pairs of wires 18A, 18B and 20A, 20B are shown in FIG. 1 installed in the connector 10.

Figure 2:
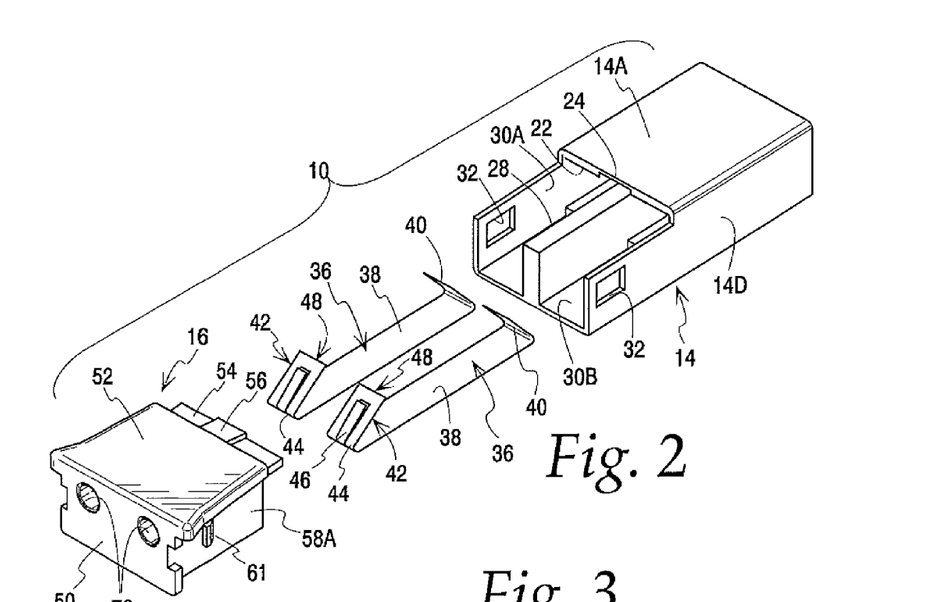
FIG. 2 is an exploded perspective view of the connector.
Figure 3:
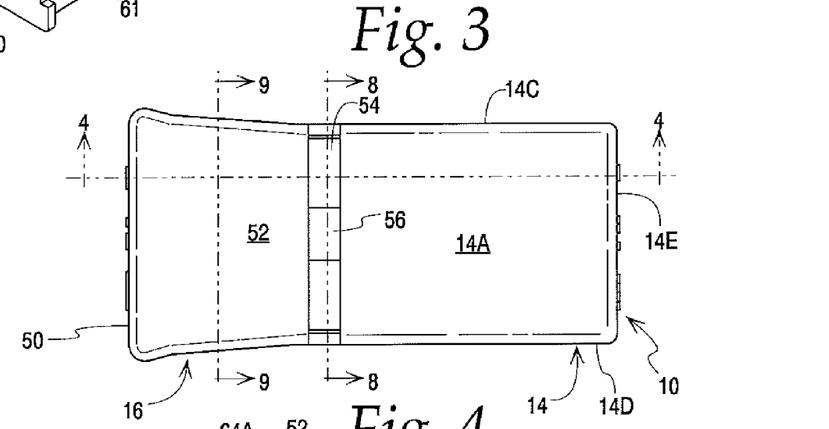
FIG. 3 is a top plan view of the connector.

Details of the housing are shown in FIGS. 1 and 2. The housing includes top and bottom walls 14A and 14B. These are joined by side walls 14C and 14D and an end wall 14E. It can be seen that the top wall 14A extends fully from one side wall to the other. However, the top wall extends from the end wall 14E only about two-thirds of the length of the bottom wall 14B, leaving an open portion of the housing. The top wall 14A terminates at an undercut 22. The center of the undercut includes a mortise 24. A step 26 is formed on the bottom wall, extending from the end wall 14E to a point aligned with the end of the top wall. A partition 28 extends the full length of the bottom wall 14B. Together with the housing walls, the partition defines first and second compartments 30A, 30B in the housing. These compartments receive the contacts and conductor pairs as will be described below. A pair of apertures 32 are formed in the side walls near the open end of the housing. These receive latches on the cap to retain the cap on the housing.

Figure 4:
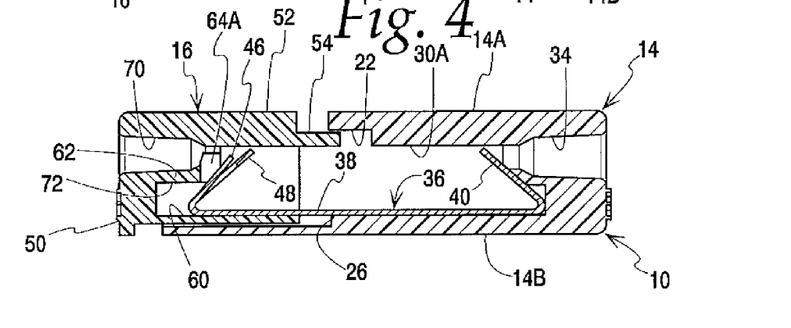
FIG. 4 is a section taken along line 4-4 of FIG. 3.

The end wall 14E of the housing has a pair of wire ports, one of which is seen in FIG. 4 at 34. The wire port preferably has a slightly tapered outer portion which receives the insulation of a wire. This tapered portion joins a necked down portion through which the bare conductor extends. As can be seen, the port 34 is in communication with the compartment, in this case 30A. Just underneath the necked down portion of the port the end wall defines a receptacle for the inner end of the contact 36.

Figures 5, 6:
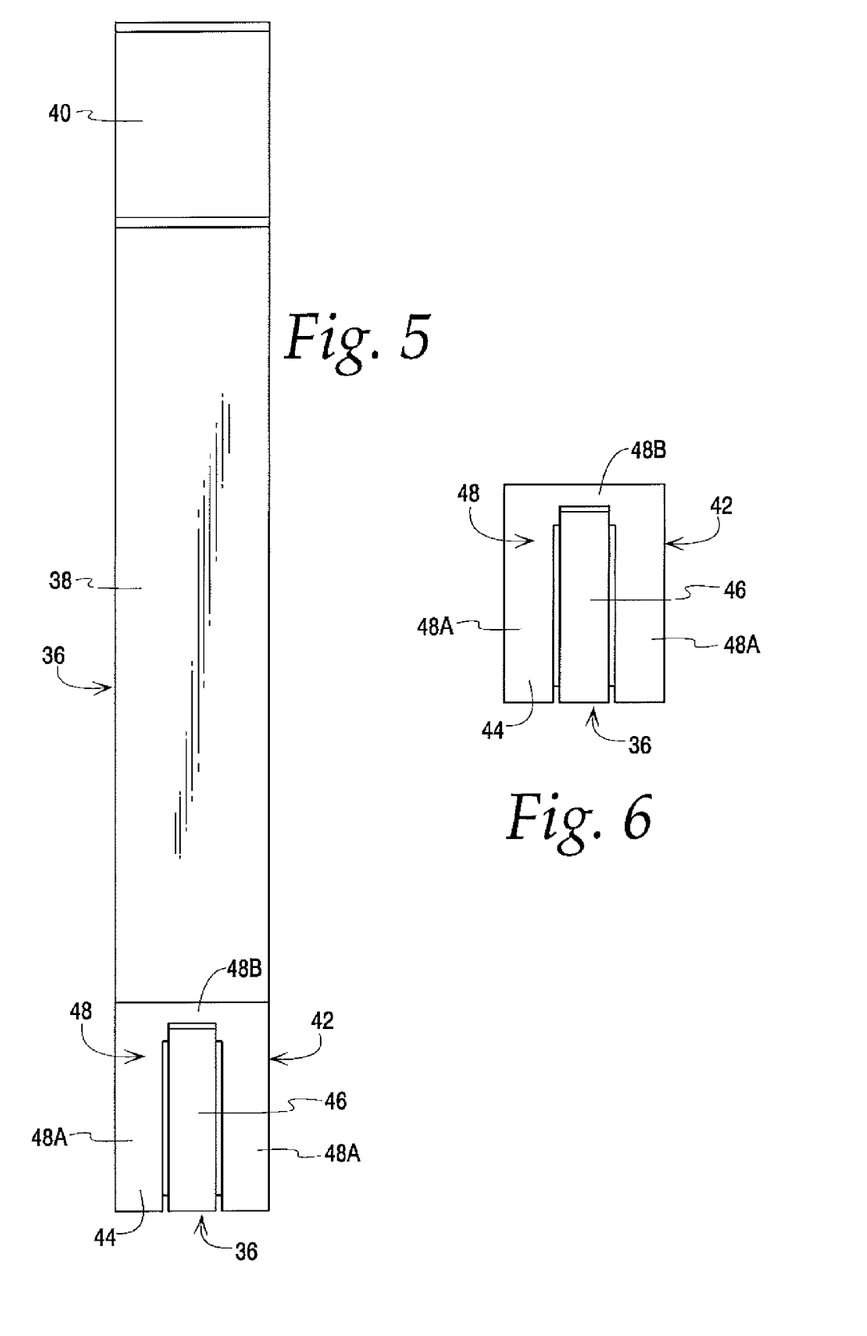
FIG. 5 is a top plan view of the contact having a split finger.
FIG. 6 is a front elevation view of the contact having a split finger.

Details of the contact 36 are shown in FIGS. 4-6. Although there is a contact in each compartment of the housing, they are identical so only one of the contacts will be described here. The contact is made of a suitable, electrically conductive material. It has an elongated plate 38. Within the closed portion of the housing 14 the plate 38 rests within a slight depression on top of the step 26. Beyond the step the plate is supported by a foot on the cap 16. At the inner end of the plate the contact has an inner finger 40 folded back on the plate at an angle of about 30° to 50°. An angle of 41° is preferable. As seen in FIG. 4, the inner finger at rest extends to a point where a portion of the finger is opposite the necked down portion of the wire port 34.

At the outer end of the plate 38 the contact 36 has an outer finger 42 which is folded back on the plate at a knuckle 44. The angle is similar to the inner finger 40. The outer finger 42 is split into multiple tines. In the preferred embodiment shown, there is a U-shaped cutout in the outer finger which defines a central, sacrificial tine 46 and a surrounding, U-shaped main tine 48. The main tine is integrally formed by a pair of legs 48A and a bight 48B. It can be seen that with this construction the tines 46 and 48 of the finger 42 can flex independently about the knuckle 44. The main tine 48 forms a slightly smaller angle with the plate than does the sacrificial tine 46. Thus, the tines are not coplanar as the sacrificial tine protrudes slightly from the plane of the main tine.

Figure 8:
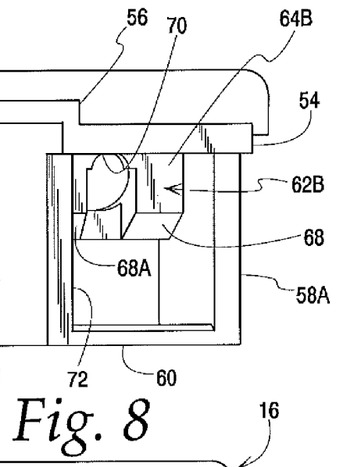
FIG. 8 is a section taken along line 8-8 of FIG. 3.
Figure 9:
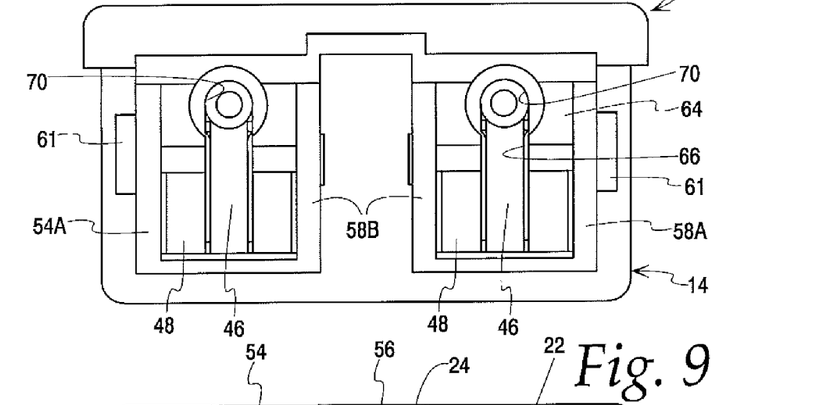
FIG. 9 is a section taken along line 9-9 of FIG. 3.

Turning now to FIGS. 2-4 and 7, the cap 16 will be described. The cap has a front wall 50 joined to a top wall 52. Extending axially from the inner end of the top wall is a ledge 54. A tenon 56 is formed on the ledge at the center. The ledge 54 interfits with the undercut 22 of the housing, as best seen in FIG. 4. The tenon similarly slidably fits into the mortise 24 of the housing (see FIG. 9). Joining the front wall 50 and top wall 52 are a pair of boxes, each defined by vertical legs 58A, 58B and a horizontal foot 60. The boxes are separated to receive the partition 28 therebetween (see FIG. 8). The feet 60 are slidable upon the bottom wall 14B of the housing. The inner edges of the feet are engageable with the step 26 of the housing to limit sliding of the cap into the housing. As mentioned above, the outer portion of the contact plate 38 and its knuckle 44 rest on the top surface of the foot. A latch 61 is formed on each of the outermost legs. The latches slidably engage the apertures 32 to prevent the cap from coming off of the housing.

Figure 7:
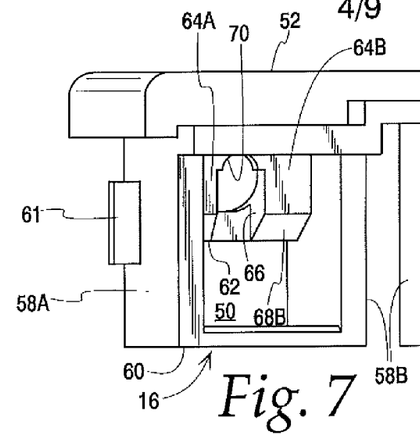
FIG. 7 is a perspective view of the interior portion of the cap.

Inside the boxes there is a release block 62. The release block is located at the upper corner of the box, where the front wall 50, top wall 52, and legs 58A, 58B meet. A pair of shoulders 64A, 64B protrude from the front edge of the release block to define a slot 66 between them. The lower corners of the shoulders have chamfers 68A, 68B. The sacrificial tine 46 fits into the slot 66 while the legs 48A of the main tine are opposite the chamfers 68A, 68B (see FIG. 8). Each release block 62 has a wire port 70 which extends through the block and through the front wall 50. The wire port 70 may be shaped like the port 34 in the housing. The port 70 opens into the slot 66 between the shoulders 64A, 64B. A contact receiving pocket 72 is defined underneath the release block 62 and shoulders 64A, 64B.

The use, operation and function of the wire connector are as follows. The normal, rest condition of the connector is as shown in FIG. 4. The cap 16 is in a retracted position wherein it is separated from the housing 14 to the maximum extent permitted by the latches 61. The fingers 40 and 42 are disposed in alignment with their respective wire ports 34 and 70. Connection of a wire 18B to the housing is straightforward. A stripped wire is inserted into the wire port 34. As the conductor enters the compartment 30A it encounters the inner finger 40 and causes it to flex downwardly to permit the conductor to pass. The flexing of the finger causes it to exert pressure on the conductor. Due to the angle of the finger, any tendency to remove the conductor causes the finger to dig into the conductor and hold it in the housing.

Figure 10:
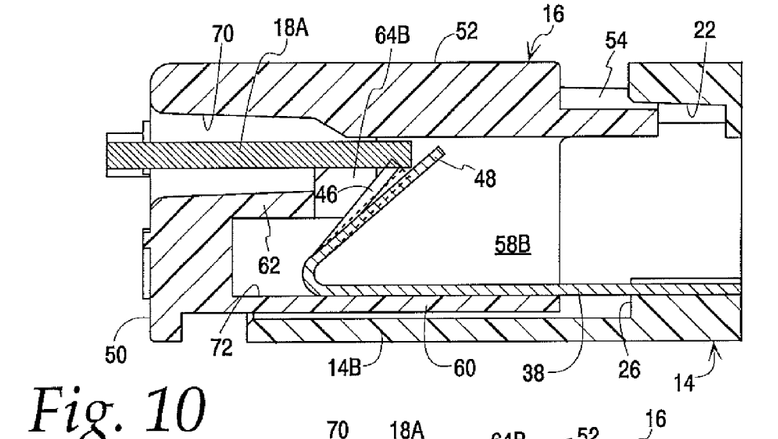
FIG. 10 is a longitudinal section through the cap and open end portion of the connector of FIG. 1, illustrating a conductor being inserted and moving the sacrificial tine and just about to make contact with the main tine.
Figure 11:
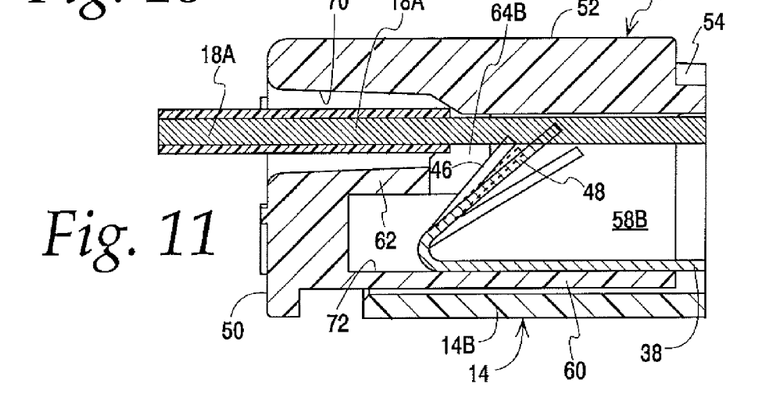
FIG. 11 is similar to FIG. 10, illustrating a conductor fully inserted and showing the movement of the tines.
Figure 12:
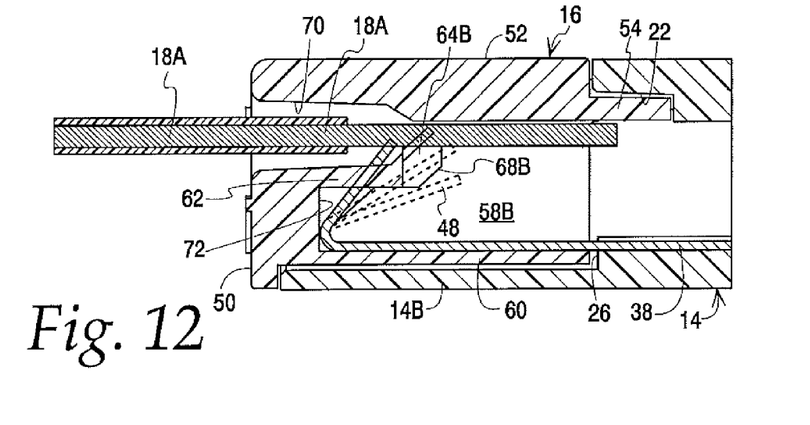
FIG. 12 is similar to FIG. 10, illustrating the cap moved to its actuated position and the resulting movement of the tines under the influence of the release mechanism.

The insertion of a wire into the other end of the compartment 30A results in a more complex series of finger movements. These are shown in FIGS. 10-12. Beginning with FIG. 10, the cap is in the retracted position so the outer finger 42 is in its rest position. As the conductor of wire 18A moves through the wire port 70 into the slot 66 it first encounters the sacrificial tine 46. When the conductor is just about to engage the sacrificial tine there may occur some arcing between the conductor and the sacrificial tine, if the circuit is live. As insertion of the conductor continues, the conductor pushes the sacrificial tine 46 downwardly from its rest position, shown in solid lines, to an active position, shown in dotted lines. Note that the conductor has not yet engaged the main tine 48. Thus, there is no possibility of arcing onto the main tine. FIG. 11 shows the conductor fully inserted and the cap still retracted. The main tine 48 has been pushed by the conductor from its rest position, shown in solid lines, to an active position, shown in dotted lines. Both the bight 48B of the main tine and the sacrificial tine 46 engage the conductor to retain it in the cap. The connection is now complete.

When it is desired to remove the wire 18A from the connector, the following actions take place. The user manually slides the cap 16 forwardly, toward the housing 14, to an actuated position. As mentioned above engagement of the foot 60 and step 26, as well as the edges of the top walls 14A and 52 of the housing and cap, limits the sliding of the cap toward the housing. As the cap moves toward the housing, the release block 62 engages the outer finger 42. Specifically, the chamfers 68A, 68B on the shoulders 64A, 64B engage the legs 48A of the main tine 48. As seen in FIG. 12, the chamfers push the main tine 48 out of engagement with the conductor. However, no arcing will occur in a live circuit upon disengagement of the main tine and conductor because the sacrificial tine 46 will still be in contact with the conductor when the main tine disengages. This is because the slot 66 will not move the sacrificial tine until after the main tine has been removed from the conductor. When the cap reaches the fully actuated position of FIG. 12, both tines will be pushed out of engagement with the conductor.

It is important to note that when the cap is in the actuated position of FIG. 12, the knuckle and a substantial portion of the finger 42 will be constrained inside the contact receiving pocket 72 of the cap. The force exerted by the tines on the underside of the release block will hold the cap in the actuated position, even if the user removes his or her hand from the cap. This permits the user to grab the old conductor for removal with the same hand used to move the cap. The cap does not have to be held by the user in the actuated position because the engagement of the pocket 72 with the tines performs that task for the user. Thus, replacement of the conductor is not a two-handed operation. It can be done with a single hand.

Once the old conductor has been removed, it is preferable for the user to retract the cap before inserting the new conductor. Insertion of the new conductor then takes place as described above in connection with FIGS. 10 and 11. However, it is not absolutely required that the cap be retracted before inserting the new conductor. Even if the new wire is inserted with the cap in the actuated position, the user need only move the cap back out after insertion and the tines will engage the new conductor to hold it in the connector. Once again the sacrificial tine will hit the conductor prior to the main tine so any arcing that may occur will be to the sacrificial tine, not the main tine. The bight of the main tine will always have a clean surface to effect the best possible electrical connection to the conductor.

Figures 13, 20:
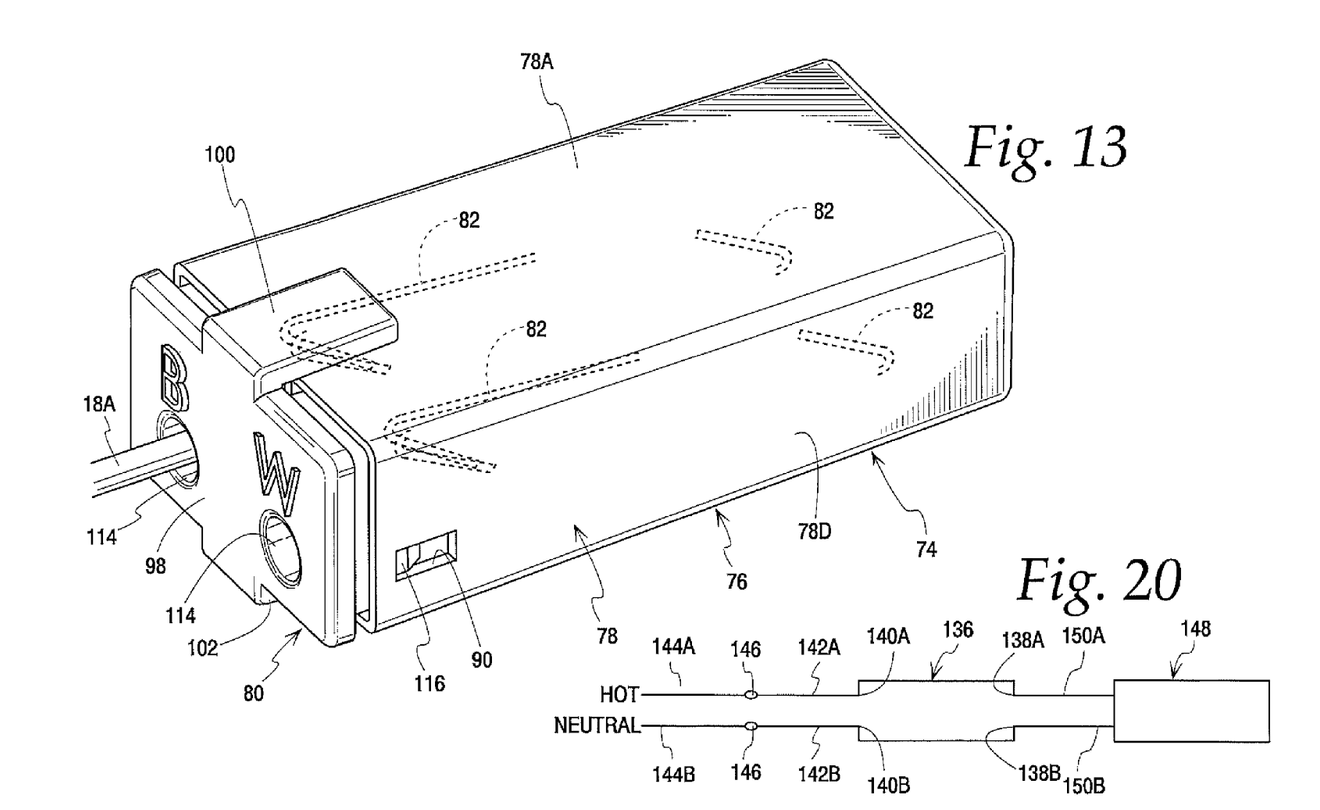
FIG. 13 is perspective view of an alternate embodiment of a releasable connector of the invention, with the internal contact shown schematically in phantom.
FIG. 20 is a schematic circuit diagram showing another embodiment of a releasable wire connector.

An alternate embodiment of the invention is illustrated in FIGS. 13-17. FIG. 13 shows the exterior of a releasable, reusable wire connector 74 according to the present invention. The connector has an enclosure 76 which includes a housing 78 and a cap 80. The cap is slidably engaged with a generally open end of the housing. While the cap can slide with respect to the housing, latches on the cap prevent complete removal of the cap from the housing. A portion of a wire 18A is shown inserted into one of the wire ports of the cap. Portions of conductive contacts 82 in the interior of the housing are also shown schematically in FIG. 13.

Figures 14, 15:
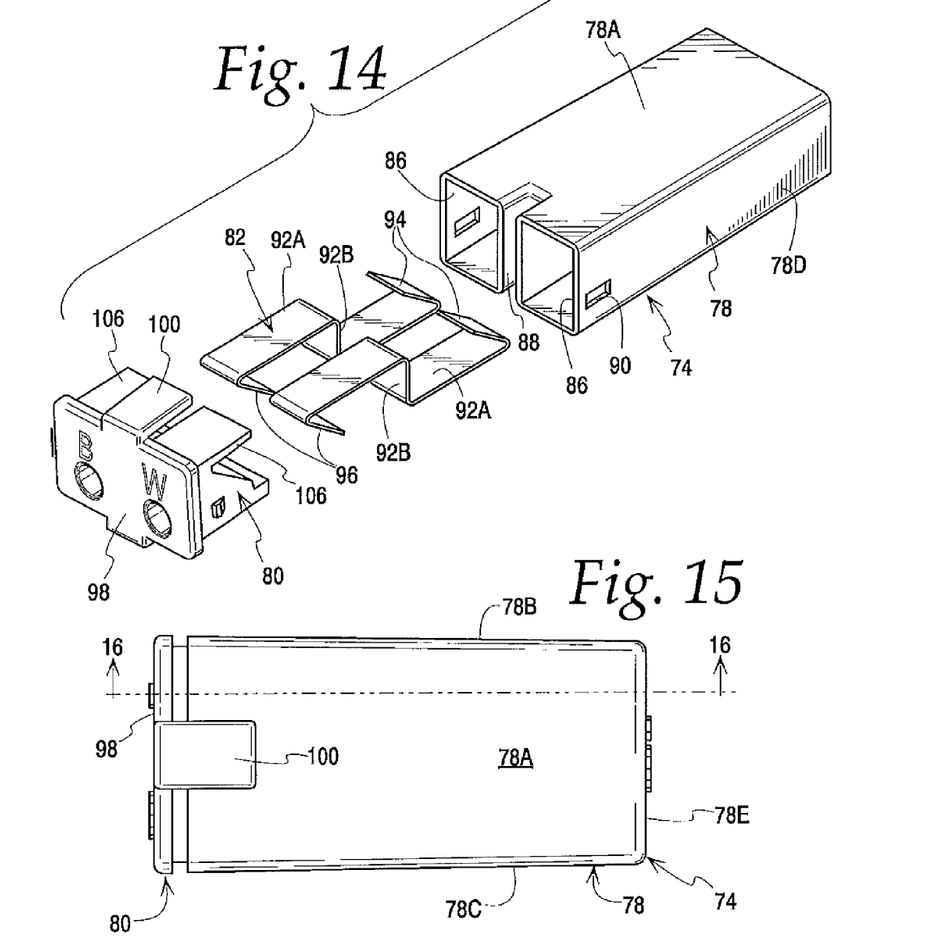
FIG. 14 is an exploded perspective view of the connector of FIG. 13.
FIG. 15 is a top plan view of the connector of FIG. 13.
Figure 16:
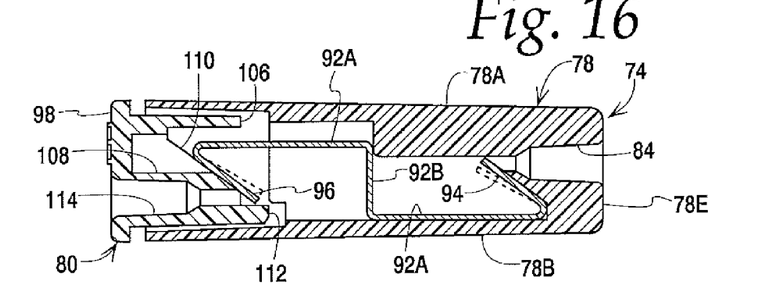
FIG. 16 is a section taken along line 16-16 of FIG. 14.
Figure 17:
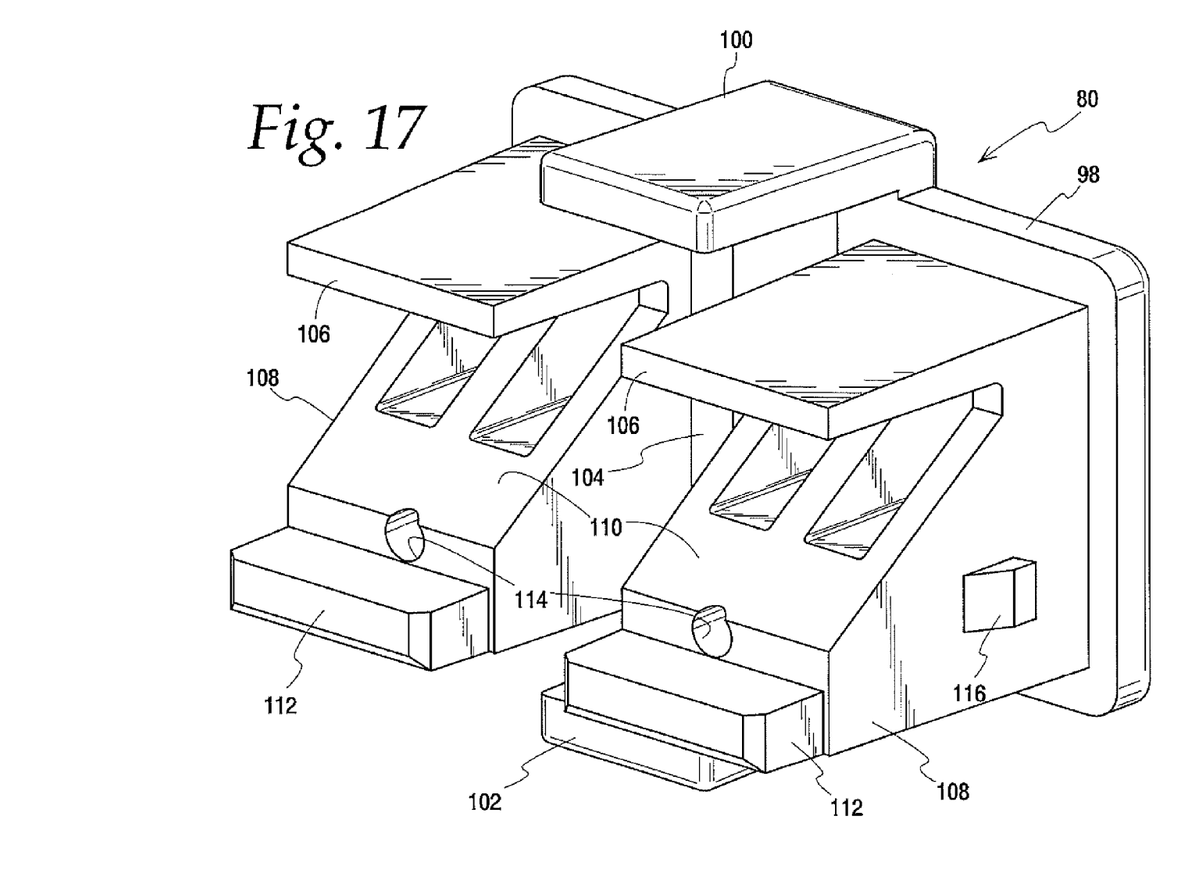
FIG. 17 is a perspective view, on an enlarged scale, of the interior portion of the cap of the alternate embodiment.

Details of the connector are shown in FIGS. 14-16. Looking first at the housing 78, it is a generally five-sided structure including top and bottom walls 78A, 78B, side walls 78C and 78D and an end wall 78E. End wall 78E has two wire ports extending therethrough, one of which is shown at 84. Each port may include a larger outer portion which accepts the insulation of a wire and a necked down inner portion that receives the stripped conductor portion of a wire. The interior end of the ports 84 open into a compartment or chamber 86 defined in the interior of the housing 78. In this embodiment there are two compartments separated by an internal partition (not shown). A wire port 84 in the end wall 78E is provided for each compartment. It will be understood that each compartment will accommodate one pair of wires to be connected and that the number of compartments could be other than the two shown in this embodiment. At the open end portion of the housing the compartments 86 are separated by a channel 88. The channel receives a locating bar on the interior of the cap as will be described below. The side walls 78C and 78D each have a rectangular aperture 90 for receiving a latch on the cap. The housing is made of a suitable electrically insulating material.

Details of the contacts 82 are shown in FIGS. 14 and 16. The contacts are made of electrically conductive material. The contact includes a body portion 92 and inner and outer fingers 94 and 96 respectively. In this embodiment the body portion has a pair of elongated plates 92A joined by a central post 92B. The fingers 94, 96 join the plates 92A at the ends thereof, disposed at an angle of about 30° to 50° to the plate, with 41° being a preferred angle.

The cap 80 has a front wall 98 joined to top and bottom guide plates 100, 102. The guide plates fit over and under the top and bottom walls 78A, 78B of the housing, respectively. A locating bar 104 (FIG. 17) on the interior of the front wall extends between the guide plates 102. The locating bar fits into the channel 88 of the housing when the cap is moved to its actuated position. Internal guide plates 106 extend rearwardly from near the top edge of the front wall. These engage the underside of the housing's top wall 78A to guide the cap's sliding movement relative to the housing. Underneath the guide plates 106 are a pair of release blocks 108. The release blocks are generally wedge-shaped and include a beveled surface 110. A toe bar 112 extends across the base of the block. Wire ports 114 extend through the front wall and release block, opening into the housing just above the toe bar. The outermost side surfaces of the release blocks carry a latch 116, which engages the apertures 90 in sliding relation to hold the cap on the housing.

The use, operation and function of the connector of FIGS. 13-17 are as follows. The normal, rest condition of the connector is as shown in FIG. 16. The cap 80 is in a retracted position wherein it is separated from the housing 78 to the maximum extent permitted by the latches 116. The fingers 96 and 98 are disposed in alignment with their respective wire ports 84 and 114. A stripped wire is inserted into the wire port 84. As the conductor enters the compartment 86 it encounters the inner finger 94 and causes it to flex downwardly to permit the conductor to pass. The flexing of the finger causes it to exert pressure on the conductor. Due to the angle of the finger, any tendency to remove the conductor causes the finger to dig into the conductor and hold it in the housing. Insertion of a second wire into the front end of the connector is similar. The conductor passes through the wire port 114, engages the outer finger 96 and pushes it upwardly, allowing the conductor to move past the finger. Pressure of the finger on the conductor prevents the conductor from pulling out of the cap.

When it is desired to remove the wires from the cap, the user pushes the cap 80 into the housing 78. The beveled surfaces 110 of the release blocks 108 engage the outer fingers 96 and push them upwardly. This relieves the pressure of the fingers on the wires, allowing them to be pulled out of the cap. Replacement wires can then be inserted in the manner described above.

Figure 18:
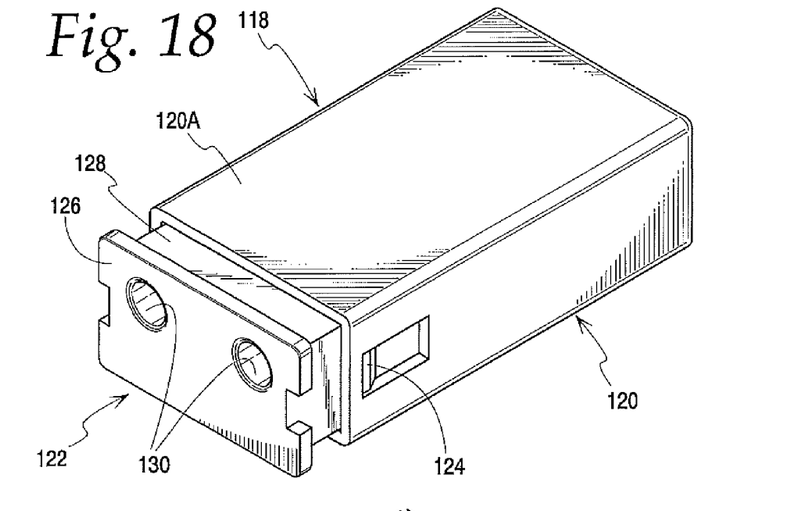
FIG. 18 is perspective view of a further alternate embodiment of a releasable connector of the present invention.
Figure 19:
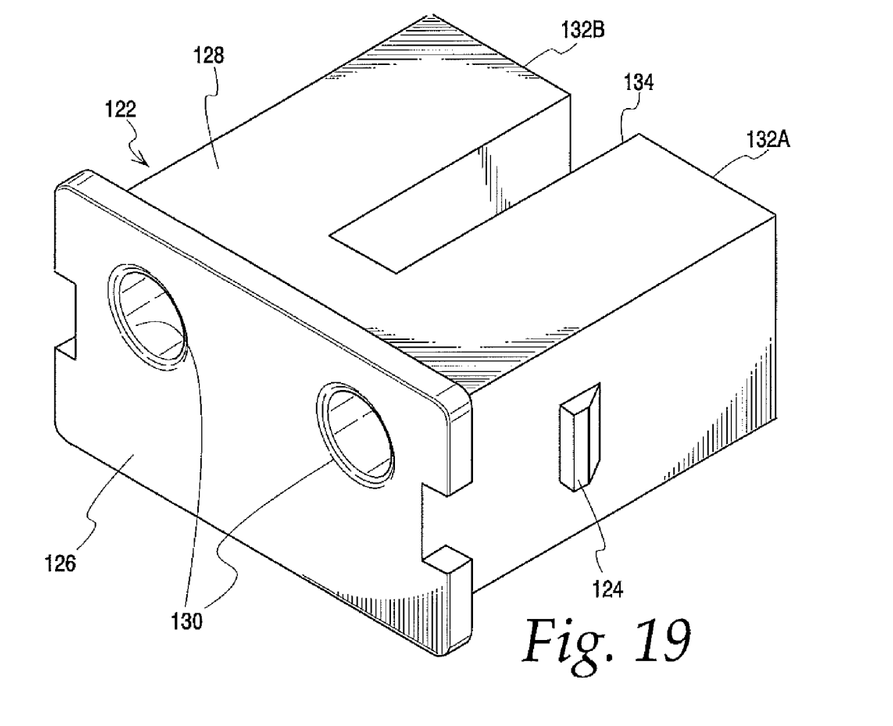
FIG. 19 is a perspective view, on an enlarged scale, of the exterior portion of the cap of the embodiment of FIG. 18.

An additional alternate embodiment of a releasable connector is shown generally at 118 in FIGS. 18 and 19. It has an enclosure including a housing 120 and a cap 122. The housing is a five-sided structure generally similar to housing 14 except the top wall 120A extends fully to the open end of the housing. The cap 122 is disposed in the open end of the housing, slidably retained therein by latches 124. The cap has a front wall 126 joined to a top wall 128. Wire ports 130 are formed in the front wall. Joining the front wall 126 and top wall 128 are a pair of boxes 132A, 132B. The boxes are separated to define a channel 134 that receives the partition inside the housing. Inside the boxes are release blocks similar to those shown at 62 in FIG. 7.

A further alternate embodiment of a releasable connector is shown generally at 136 in FIG. 20. The enclosure of this connector may the same as enclosure 12 in FIGS. 1-12. Thus, the enclosure will include releasable wire contacts indicated schematically at 138A, 138B and non-releasable contacts at 140A, 140B. Connector 136 includes pigtail wires 142A, 142B permanently joined to the non-releasable contacts 140A, 140B. The non-releasable contacts may be the push-in type described above, or they could be some other type of permanent connection such as push-in plus solder, push-in plus ultrasonic welding, insulation displacement connectors, crimp connectors, set screw connectors, or any other known permanent connector.

This arrangement of an enclosure plus pigtail wires provides convenient way to replace failed circuit elements in live circuits without exposing the conductors of the live circuit. In an original installation the free ends of the pigtail wires 142A, 142B may be connected to hot and neutral supply lines 144A, 144B by any suitable wire connectors 146. A circuit element such as a fluorescent light ballast 148 has its own lead wires 150A, 150B permanently connected to the element. The free ends of the lead wires are attached to the releasable contacts 138A, 138B of the connector 136. When the ballast, or other circuit element, fails it can be removed from the circuit by releasing the contacts 138A, 138B and removing the lead wires of the failed unit. A new unit can then be installed and its lead wires placed in the contacts 138A, 138B. Due to the construction of the enclosure 12, the person performing this operation will never be exposed to live circuit components.

While the preferred form of the invention has been shown and described herein, it should be realized that there may be many modifications, substitutions and alterations thereto. For example, while the housing shown accommodates connections of two wire pairs, other numbers of compartments and contacts could be used to connect different numbers of wire pairs. Also, a movable cap could be placed at each end of the housing such that all wires are releasable. A further alternate embodiment could have the release block formed separately from the cap. In such an arrangement the cap may or may not be slidable relative to the housing, so long as the release block is slidable relative to the contact finger to selectively restrain the finger from biasing against an inserted wire. As mentioned above a holding feature may be built into one or both of the cap and housing to hold the cap in the actuated position. Or the holding feature may involve a cap-to-spring interaction. Or the holding feature may be provided by a friction fit between the cap and housing. Yet another alternate embodiment could arrange the release block's contact receiving pocket so that it would not retain the contact finger. Rather, the finger would create an axial bias on the cap such that it would not stay in the actuated position but instead would always move back to the retracted position once the user releases it.

Further alternate embodiments might include a cap that pivots or rocks relative to the housing, rather than sliding. Also, instead of a release mechanism built into the cap, the release mechanism could be built into the housing where it could be actuated either directly by the user or indirectly by movement of the cap. Some space saving could be obtained by stacking the two wires being joined. That is, rather than having the axes of the connected wires being coaxial as shown, the axes may be one above the other in an overlapping arrangement. Obviously this would require reconfiguring the spring. Finally, all the wire ports could be on one side of the enclosure only with only a single pole (like a traditional push-in connector) but with the release features shown. The release feature could be arranged to release the wires individually or all at once.

We claim:

1. A releasable wire connector, comprising:
   an enclosure which includes a housing and a cap which are engaged with one another for selective movement between actuated and retracted positions;
   at least one compartment defined in the enclosure;
   first and second wire ports defined in the enclosure, each wire port opening into the compartment and defining an axis;
   a contact mounted in the compartment and having a pair of flexible fingers, one finger being opposite each wire port, each finger being angled with respect to the axis of the wire port; and
   at least one release block disposed in the compartment opposite one of the fingers, the release block being movable with one of the cap and housing between an actuated position and a retracted position, the release block engaging the finger when the cap and housing are in the actuated position to bias the finger away from the axis of the wire port and the release block releasing the finger when the cap and housing are in the retracted position.

2. The releasable wire connector of claim 1 wherein the enclosure further comprises a contact receiving pocket defined in one of the housing and cap, the contact receiving pocket being engageable with the contact when the cap and housing are in the actuated position to retain the cap and housing in the actuated position.

3. The releasable wire connector of claim 1 wherein at least one of the contact fingers comprises a sacrificial tine and a main tine.

4. The releasable wire connector of claim 1 wherein the release block is connected to the cap.

5. The releasable wire connector of claim 4 wherein the release block has a chamfered surface engageable with the contact finger.

6. The connector of claim 1 wherein the cap and housing are slidably engageable with one another.

7. The releasable wire connector of claim 1 further characterized in that the enclosure comprises first and second compartments, each compartment communicating with its own first and second wire ports, and each compartment having a contact mounted therein, each contact having a pair of flexible fingers, one finger being opposite each wire port in the respective compartments, each finger being angled with respect to the axis of its associated wire port; and
   at least one release block disposed in each of the first and second compartments opposite one of the fingers, the release blocks being movable with one of the cap and housing between an actuated position and a retracted position, the release blocks engaging the fingers when the cap and housing are in the actuated position to bias the fingers away from the axis of its respective the wire port and the release blocks releasing the fingers when the cap and housing are in the retracted position.

8. The releasable wire connector of claim 1 wherein the cap further comprises a foot slidably engageable with the housing and supporting a portion of the contact thereon.

9. The releasable wire connector of claim 1 further comprising a pigtail wire engaged with the other of the contact fingers not opposite the release block.

10. A releasable wire connector, comprising:
    an enclosure which includes a housing and a cap which are engaged with one another for selective movement between actuated and retracted positions;
    at least one compartment defined in the enclosure;
    first and second wire ports defined in the enclosure, each wire port opening into the compartment and defining an axis;
    a contact mounted in the compartment for selectively releasable engagement with wires inserted through the wire ports into the compartment, the contact retaining inserted wires when the housing and cap are in the retracted position and releasing inserted wires when the housing and cap are in the actuated position; and
    at least two of the cap, housing and contact engaging one another when the cap and housing are placed in the actuated position to retain them in the actuated position.

11. The releasable wire connector of claim 10 wherein one of the housing and cap have a contact receiving pocket defined therein, the contact receiving pocket being engageable with the contact when the cap and housing are in the actuated position to retain the cap and housing in the actuated position.

12. The releasable wire connector of claim 11 wherein the contact receiving pocket is formed in the cap.

13. The releasable wire connector of claim 12 further comprising at least one release block mounted on the cap and disposed in the compartment opposite one of the fingers, the release block being movable with the cap between an actuated position and a retracted position, the release block engaging the contact when the cap and housing are in the actuated position to bias the contact away from the axis of the wire port and the release block releasing the contact when the cap and housing are in the retracted position.

14. The releasable wire connector of claim 13 wherein the cap further comprises a foot and the contact receiving pocket is defined between the release block and the foot.

15. A wire connector, comprising:
    an enclosure having at least one compartment and first and second wire ports defined therein, each wire port opening into the compartment;
    a contact mounted in the compartment and having a sacrificial tine and a main tine, both tines being selectively releasably engageable with wires inserted through the wire ports into the compartment, the sacrificial tine being disposed in relation to the wire port such that a wire inserted through the port will make contact first with the sacrificial tine and subsequently with the main tine.

16. The wire connector of claim 15 further characterized in that the main tine is disposed in relation to the sacrificial tine such that a wire retracted from the wire port will first break contact with the main tine and subsequently with the sacrificial tine.

17. The wire connector of claim 15 wherein the contact has a base and the sacrificial tine and main tine are connected to the base with the sacrificial tine being located closer to the wire port than the main tine.

18. The wire connector of claim 17 wherein the base is a plate and the sacrificial and main tines are disposed at different angles to the plate, the angle of the main tine to the plate being less than the angle of the sacrificial tine to the plate.

19. The wire connector of claim 18 wherein the main tine comprises a pair of legs joined by a bight.

20. The wire connector of claim 19 wherein the sacrificial tine is located between the legs of the main tine and spaced therefrom.

21. A releasable wire connector, comprising:
   an enclosure having at least one compartment and first and second wire ports defined therein, each wire port opening into the compartment;
   a pigtail wire having a stripped end inserted through the first wire port and into the compartment, the other end of the pigtail wire extending from the enclosure; and
   a contact mounted in the compartment, the contact having a first portion engaging the stripped end of the pigtail wire and permanently retaining the pigtail wire in the first wire port, the contact having a second portion for selectively releasable engagement with a wire inserted through the second wire port into the compartment.

22. The releasable wire connector of claim 21 further comprising third and fourth wire ports defined in the enclosure and opening into the compartment, a second pigtail wire with a stripped end inserted through the third wire port of the compartment, the other end of the pigtail wire extending from the enclosure, and a second contact mounted in the compartment, the second contact having a first portion engaging the stripped end of the second pigtail wire and permanently retaining the second pigtail wire in the third wire port, the second contact having a second portion for selectively releasable engagement with a wire inserted through the fourth wire port into the compartment.

23. The releasable wire connector of claim 21 wherein the enclosure comprises first and second compartments, each compartment communicating with its own first and second wire ports, and each compartment having a pigtail wire with a stripped end inserted through the first wire port of the compartment, the other end of the pigtail wire extending from the enclosure and each compartment having a contact mounted therein, the contact having a first portion engaging the stripped end of the pigtail wire and permanently retaining the pigtail wire in the first wire port, the contact having a second portion for selectively releasable engagement with a wire inserted through the second wire port into the compartment.

* * * * *